United States Patent [19]

Breuer et al.

[11] Patent Number: 4,983,761

[45] Date of Patent: Jan. 8, 1991

[54] PROCESS FOR THE PREPARATION OF HIGH-BOILING ACRYLATES AND METHACRYLATES

[75] Inventors: Siegfried Breuer, Frankfurt am Main; Heinz Delle, Bad Homburg; Udo Ruldolph, Hanau, all of Fed. Rep. of Germany

[73] Assignee: Degussa Aktiengesellschaft, Frankfurt am Main, Fed. Rep. of Germany

[21] Appl. No.: 417,558

[22] Filed: Oct. 5, 1989

[30] Foreign Application Priority Data

Oct. 22, 1988 [DE] Fed. Rep. of Germany ....... 3836093

[51] Int. Cl.$^5$ .............................................. C07C 67/02
[52] U.S. Cl. ..................................... 560/217; 560/218
[58] Field of Search ................................. 560/217, 218

[56] References Cited

U.S. PATENT DOCUMENTS 4,791,221 12/1988 Gabillet ................................ 560/217

FOREIGN PATENT DOCUMENTS 2317226 4/1973 Fed. Rep. of Germany .
2744641 10/1977 Fed. Rep. of Germany .

*Primary Examiner*—Paul J. Killos
*Attorney, Agent, or Firm*—Cushman, Darby & Cushman

[57] ABSTRACT

A method of preparing high-boiling acrylates and methacrylates with low color indices by means of the transesterification of methyl acrylate and methacrylate with polyvalent alcohols is known ways which is characterized in that the product is subjected, after the separation of the catalyst, to a short-path evaporation at a bottom temperature of 110° to 170° C. and a pressure of 0.01 to 10 mbar.

2 Claims, No Drawings

PROCESS FOR THE PREPARATION OF HIGH-BOILING ACRYLATES AND METHACRYLATES

The present invention relates to a method of preparing high-boiling acrylates and methacrylates with low color indices and high purity. The products are prepared by means of the transesterification of (meth)acrylic acid methyl ester with appropriate alcohols with the addition of alkali, alkaline-earth, titanium or zirconium alcoholates as catalysts and polymerization inhibitors as well as entraining agents for expelling the methanol released during the reaction.

BACKGROUND OF THE INVENTION

Variations of the type of method described are known. However, these methods generally seek only for as high a conversion as possible (DE-OS 28 05 702) and do not consider a distillative purification in the case of the higher-boiling acrylates and methacrylates, e.g. trimethylol propane trimethacrylate Published German Patent Application DE-OS 27 44 641.

Apha color indices according to Hazen of 15 (DIN 55409) can be achieved in the preparation of higher-molecular alkyl acrylates and alkyl methacrylates if the transesterification is carried out according to Published German Patent Application DE-OS 23 17 226 in the presence of a small amount of absorbent carbon as polymerization inhibitor. However, if the description of this patent is followed, the desired degrees of purity can not be achieved by means of a vacuum distillation of the type suggested in British Patent 962,928.

SUMMARY OF THE INVENTION

The object of the present invention is to provide a method of preparing high-boiling acrylates and methacrylates with even lower color indices and especially high purity.

These and other objects are achieved by a method of preparing high-boiling acrylates and methacrylates with low color indices by means of the transesterification of methylacrylate or methacrylate with polyvalent alcohols in known manner in which the product is subjected, after the separation of the catalyst, to a short-path evaporation at a bottom temperature of 110° to 170° C. and at a pressure of 0.01 to 10 mbar.

The high-boiling acrylates and methylacrylates which are prepared according to the present invention are compounds whose boiling point under normal pressure exceeds 160° C., especially 190° C., and can reach 400° C. Higher-molecular weight esters which can be prepared in accordance with the invention with a molecular weight up to approximately 400 correspond to the general formula I

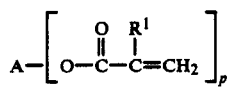

in which
R¹ represents hydrogen or methyl,
when P is 3, A represents a straight-chain or branched group containing 4 to 6 carbon atoms and optionally containing 1 or 2 oxygen bridges, or
when P is 2, A represents a straight-chain or branched group containing 2 to 8 carbon atoms and 0 or 2 to 3 oxygen bridges.

Esters of the alcohols 1,4 butane diol, tripropylene glycol, triethylene glycol, sym. dimethylethylene glycol, tetraethylene glycol, 2,2,4-trimethyl-1,3-propane diol, trimethylol ethane and trimethylol propane are preferred.

Methods for transesterification are known, as has already been described in the BACKGROUND OF THE INVENTION. The general procedure used is to react the methyl esters with the alcohols at temperatures of 60° to 140° C. in the presence of suitable transesterification catalysts and polymerization inhibitors.

Especially phenothiazine and/or its derivatives, preferably methylene blue, have proven themselves useful in the present method as the latter material. They are used in a concentration of 50 to 2000 ppm relative to the reaction mixture alcohol/(meth-)acrylate.

The methyl alcohol produced during the reaction is drawn off as an azeotropic mixture with an entraining agent such as e.g. n-hexane or cyclohexane in a continuous manner and preferably fed into a wash-water circuit closed over a phase-separation vessel.

The methanol goes over practically quantitatively into the aqueous phase whereas the hexane phase is returned to the column head in a thermal exchange with the head condensate.

The workup of the wash-water phase takes place according to a known procedure.

The transesterification reaction is preferably carried out while passing oxygen-containing gases, preferably air, through the reaction vessel.

After the end of the reaction, the transesterification catalyst is separated in a suitable manner. Alcoholates such as e.g. alkyl titanates are hydrolyzed and the precipitating hydroxide filtered off, optionally with the addition of filter aids. Water produced during the saponification is removed as an azeotrope.

If lithium salts are used as transesterification catalysts, appropriate measures are to be taken (DE-OS 27 44 641).

After separation of the catalyst, distillative purification according to the present invention is carried out. In the first step of this purification, for example, excess starting products and the entraining agent are separated via a falling-film evaporator.

The raw product obtained in this manner is subjected, in the second step, to a short-path evaporation or short-path distillation.

If entrained traces e.g. of the stabilizer methylene blue should still be contained in the pure distillate, they can be removed without problems during passage through an activated-carbon filter.

Products are obtained in this manner with a purity of greater than 98 % (gas chromatographic analysis) and an Apha number from 0 to 5.

It is of course also possible to purify lower-boiling esters in this manner.

DETAILED DESCRIPTION OF PREFERRED EMBODIMENTS

The invention is illustrated by the following example:

EXAMPLE 600 g triethylene glycol (TEG), 1200 g methyl methacrylate (MMA), 0.14 g hydroquinone monomethyl ether (MEHQ), 1.0 g methylene blue and 300 g n-hexane are placed into a 3-liter double-jacket glass reactor (heating/cooling jacket) with a 10-bottom column set on top. The mixture is heated to the boiling temperature in order to first remove traces of water contained in the mixture azeotropically with n-hexane. The head condensate runs into a wash-water circuit closed over a phase-separation vessel in which the removed water remains while the n-hexane runs over out of the separating vessel and is returned back to the head of the column. Approximately 5 liters per hour atmospheric oxygen is to be fed into the reaction mixture for stabilization. After the dewatering phase, 25 g alkyl titanate are added to the reaction mixture, which causes the transesterification reaction to start. The released methanol forms an azeotrope which boils at approximately 50° C. with the n-hexane, so that methanol is rapidly entrained into the column head, whose temperature is approximately 68° C. The head condensate (hexane+methanol) is completely fed into the previouslymentioned wash circuit. The methanol passes practically quantitatively into the aqueous phase while the hexane phase formed is guided back to the column head in a thermal exchange with the head condensate. The wash-water phase is enriched with methanol in the course of the transesterification reaction and should be continuously removed when the concentration of methanol reaches 50% with concurrent introduction of fresh water into the circuit. The complete conversion of the TEG may be determined by means of gas chromatographic analysis. At the end of the reaction (reaction temperature approximately 120° C.), the reaction mixture is cooled to approximately 80° C. 50 g 10 % $H_2SO_4$ is added to hydrolyze the alkyl titanate which requires approximately 30 minutes. 20 g $CaCO_3$ are then added. Titanium hydroxide and $CaSO_4$ are formed. Free residual water is removed azeotropically after a repeated heating—as in the dewatering already described. The solid portion present in the reaction mixture can be quantitatively separated with a conventional filter, optionally after the addition of filter aids.

The filtrate is fed to a distillation apparatus. The distillation takes place in two stages. Excess MMA and hexane are separated in the first stage, via a falling-film evaporator down to a residual content of <0.2 % in the crude product (bottom). The distillation takes place at approximately 120° C. runoff temperature of the crude product and approximately 30 mbar operating pressure. The distillate (MMA and hexane) is recycled into the next transesterification batch. The crude product is finally subjected in the second stage at approximately 0.1 mbar and approximately 150° C. (bottom runoff temperature) to a shortpath distillation. The bottom, approximately 5 % of the amount of distillate, is returned into the next transesterification batch. After cooling, the pure distillate is passed through an activated-carbon filter into the product tank, in order to adsorb any entrained traces of methylene blue. The product has a purity of greater than 98 % (GC). The Apha number is 0./0.5.

What is claimed is:

1. In a method of preparing a member of the group consisting or high-boiling acrylates and methacrylates, whose boiling point under normal pressure exceeds 160° C. with an Alpha number from 0 to 5 corresponding to formula I

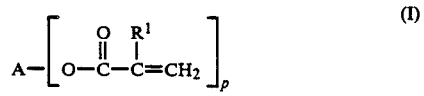

where in
R' represents hydrogen or methyl,
when p is 3, A represents a straight-chain or branched group containing 4 to 6 carbon atoms and which may contain 1 or 2 oxygen bridges, or
when p is 2, A represents a straight-chain or branched group containing 2 to 8 carbon atoms and 0 or 2 to 3 oxygen bridges, by means of the transesterification of a member of the group consisting of methyl acrylate and methyl methacrylate with a polyvalent alcohol;
the improvement in which the reaction mixture of the transesterification is separated from a catalyst and thereafter is subjected to a flash distillation at a bottom temperature of 110° to 170° C. and a pressure of 0.01 to 10 mbar.

2. A method as set forth in claim 1 including purifying distillate from the flash distillation with an activated-carbon filter.

* * * * *